(12) United States Patent
Ohmura et al.

(10) Patent No.: US 7,810,994 B2
(45) Date of Patent: Oct. 12, 2010

(54) X-RAY IMAGING APPARATUS

(75) Inventors: Satoru Ohmura, Kamakura (JP);
Masaaki Kobayashi, Shimotsuke (JP);
Katsushi Kato, Kawasaki (JP);
Hiroyuki Ichiyoshi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/551,148

(22) Filed: Aug. 31, 2009

(65) Prior Publication Data
US 2010/0054422 A1 Mar. 4, 2010

(30) Foreign Application Priority Data
Sep. 1, 2008 (JP) ............................. 2008-223495

(51) Int. Cl.
*H05G 1/02* (2006.01)
(52) U.S. Cl. ...................................... 378/196; 378/198
(58) Field of Classification Search ................. 378/102, 378/196–198
See application file for complete search history.

(56) References Cited

U.S. PATENT DOCUMENTS

| 2,764,694 | A | * | 9/1956 | Kinzer | 378/190 |
| 6,543,936 | B2 | * | 4/2003 | Feldman | 378/191 |
| 6,754,306 | B2 | * | 6/2004 | Cho et al. | 378/102 |
| 2005/0058257 | A1 | * | 3/2005 | Fischer et al. | 378/196 |
| 2009/0129554 | A1 | * | 5/2009 | Denley | 378/198 |

FOREIGN PATENT DOCUMENTS

| JP | 2000-51189 A | 2/2000 |
| JP | 2004-208716 A | 7/2004 |

* cited by examiner

*Primary Examiner*—Irakli Kiknadze
(74) *Attorney, Agent, or Firm*—Canon U.S.A., Inc. IP Division (57) ABSTRACT

An X-ray imaging apparatus includes an X-ray tube, an X-ray generation control unit configured to control the X-ray tube with a controller and a power supply, and a holding unit configured to hold the X-ray tube. The holding unit includes two support legs to be spread at an arbitrary angle, and a connecting portion configured to turnably connect upper ends of the support legs. The holding unit holds the X-ray tube near the connecting portion.

7 Claims, 10 Drawing Sheets

FIG. 17

# X-RAY IMAGING APPARATUS

BACKGROUND OF THE INVENTION

1. Field of the Invention

The present invention relates to an X-ray imaging apparatus that obtains an X-ray image from X-rays transmitted through a subject, and more particularly, to a movable X-ray imaging apparatus for use in image taking performed, for example, at home or at the time of disaster.

2. Description of the Related Art

There are known movable X-ray imaging apparatuses that are moved to the bedside in a patient's room to take an X-ray image of a subject in a state in which an X-ray device is mounted on a carriage. In these X-ray imaging apparatuses, a storage box storing an X-ray film cassette and the like is often provided integrally with an X-ray control unit.

Japanese Patent Laid-Open No. 2000-51189 proposes a movable imaging system in which an X-ray control unit and a storage unit storing an X-ray film cassette are connected detachably.

Japanese Patent Laid-Open No. 2004-208716 proposes a digital X-ray imaging apparatus that does not use an X-ray film. For example, CR (Computed Radiography) using a photostimulable phosphor plate as an X-ray detector, and DR (Digital Radiography) in which a taken image is instantaneously displayed on a monitor are used. A movable imaging system in which these methods are applied to a mobile X-ray imaging apparatus has been proposed. An X-ray generation unit and a base unit are provided in a detachable manner. The base unit includes a power supply for the X-ray generation unit, and a high-voltage generator for applying a voltage to an X-ray tube in the X-ray generation unit.

Thus, a digital examination car in which a thin, lightweight, and portable FPD (Flat Panel Detector) is mounted can immediately perform image recognition and perform an image taking operation again, and development and cassette replacement during another image taking operation and multidirectional image taking operation are unnecessary. It is therefore possible to reduce the burden on a subject and an inspector and to achieve a high investigation accuracy.

In the movable X-ray imaging apparatus disclosed in Japanese Patent Laid-Open No. 2004-208716, however, an X-ray tube is held via a support and an arm having rigidity and provided in the main body of the apparatus, and the position and angle of the X-ray tube are changed by the support and the arm. The support and the arm increase the weight of the apparatus.

Further, the X-ray tube and the support protrude from the apparatus. To balance the apparatus against the protrusion, the apparatus needs to have a certain base area. Moreover, at least three wheels are necessary for stability. In addition, while the apparatus has a self running function to improve operability in response to the increase in weight, the self running function needs a power supply and a motor. This further increases the weight of the apparatus.

Consequently, size and weight reduction of the apparatus is difficult. In particular, it is difficult to use the apparatus in a site where portability is needed, for example, in a disaster area or at home for medical care. Further, there is much irregular ground in the disaster area, and high operability is required so as to quickly and precisely align the apparatus in accordance with various image taking conditions for the site.

Assuming that the X-ray imaging apparatus is used in an environment where a facility, such as an X-ray protective barrier, for preventing exposure to X-rays is not provided, it is preferable that the apparatus have less danger of exposure of parts of a subject other than a target part to be exposed, an X-ray photographer, and other persons.

SUMMARY OF THE INVENTION

The present invention provides an X-ray imaging apparatus that improves portability by size and weight reduction, allows quick installation and alignment, and reduces the risk of exposure.

In order to achieve the above object, for example, an X-ray imaging apparatus of the present invention includes the following arrangement.

The X-ray imaging apparatus includes an X-ray tube; an X-ray generation control unit configured to control the X-ray tube with a controller and a power supply; and a holding unit configured to hold the X-ray tube. The holding unit includes at least two support legs to be spread at an arbitrary angle, and a connecting portion configured to turnably connect upper ends of the support legs, the holding unit holding the X-ray tube near the connecting portion.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention, and together with the description, serve to explain the principles of the invention.

DESCRIPTION OF THE PREFERRED EMBODIMENTS

Preferred embodiments of the present invention will be described in detail in accordance with the accompanying drawings.

First Embodiment

Figure 1:
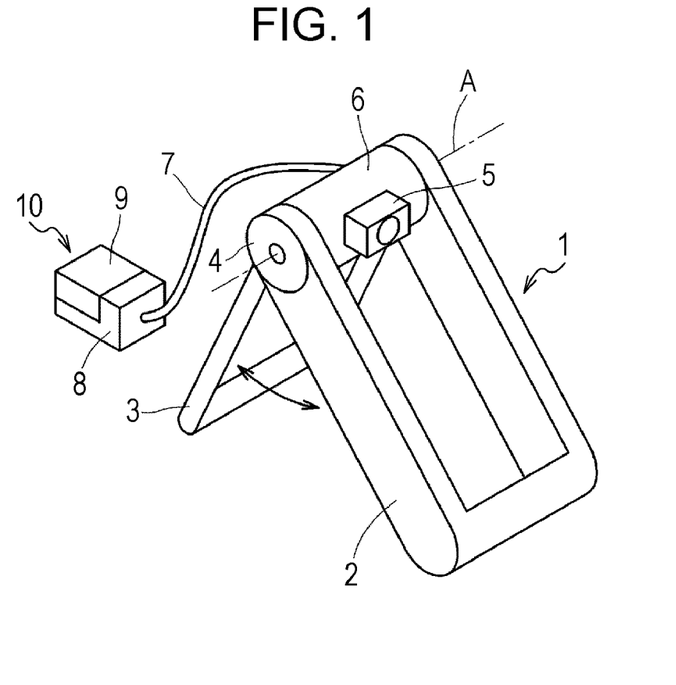
FIG. 1 is a perspective view of an X-ray imaging apparatus according to a first embodiment.

FIG. 1 is a perspective view of an X-ray imaging apparatus according to a first embodiment. In the X-ray imaging apparatus, a holding unit 1 includes two support legs 2 and 3. In each of the support legs 2 and 3, two supports are connected at a lower side to form a U-shape. Upper ends of the support legs 2 and 3 are turnably connected via a connecting portion 4, whereby the support legs 2 and 3 can be spread. The spread angle between the support legs 2 and 3 can be arbitrarily set by the frictional force of the connecting portion 4. A holding member 6 turnable on an axis A is provided at the top of the holding unit 1. The holding member 6 holds an X-ray tube 5 so that the X-ray tube 5 can emit X-rays at an arbitrary angle.

The X-ray tube 5 is connected to an X-ray generation control unit 10 via a cable 7. The X-ray generation control unit 10 includes a controller 8 for controlling X-ray radiation by the X-ray tube 5, and a power supply 9 for supplying power for X-ray radiation.

By virtue of the above-described structure, the X-ray imaging apparatus is made compact and is improved in portability by closing the support legs 2 and 3 during movement when carried. In contrast, by spreading the support legs 2 and 3 during image taking, the X-ray tube 5 can be held by the holding member 6. The height of the X-ray tube 5 can be changed by adjusting the spread angle of the support legs 2 and 3.

Figure 2:
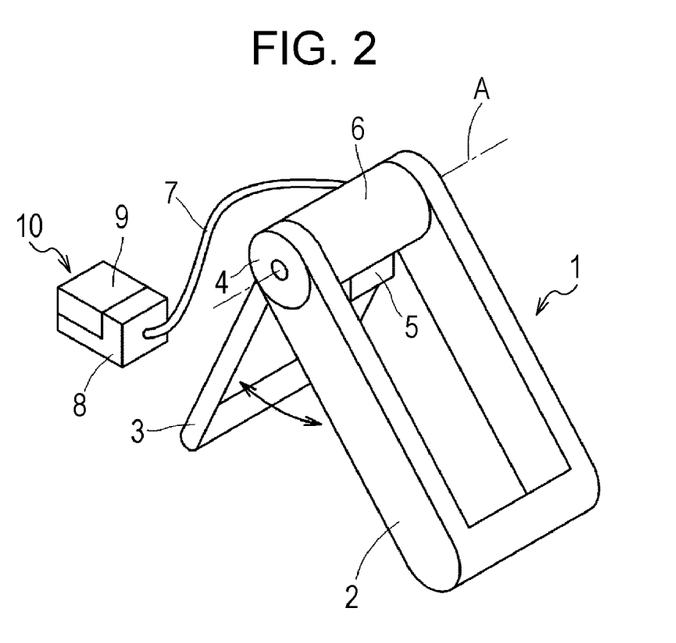
FIG. 2 is a perspective view of the X-ray imaging apparatus according to the first embodiment.

FIG. 2 is a perspective view illustrating another use state of the X-ray imaging apparatus. The X-ray tube 5 is turned down on the axis A relative to the connecting portion 4 to emit X-rays downward.

Second Embodiment

Figure 3:
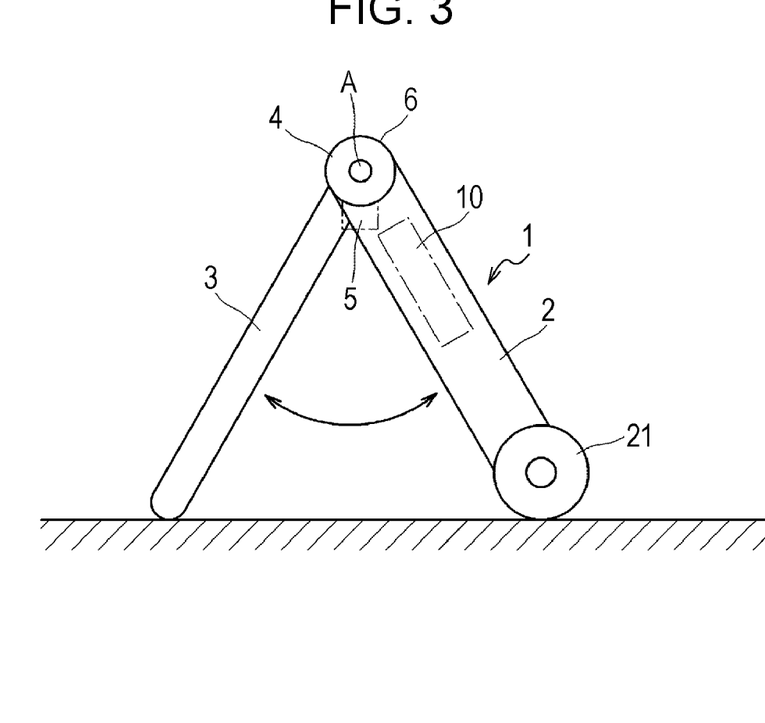
FIG. 3 is a side view of an X-ray imaging apparatus according to a second embodiment.
Figure 4:
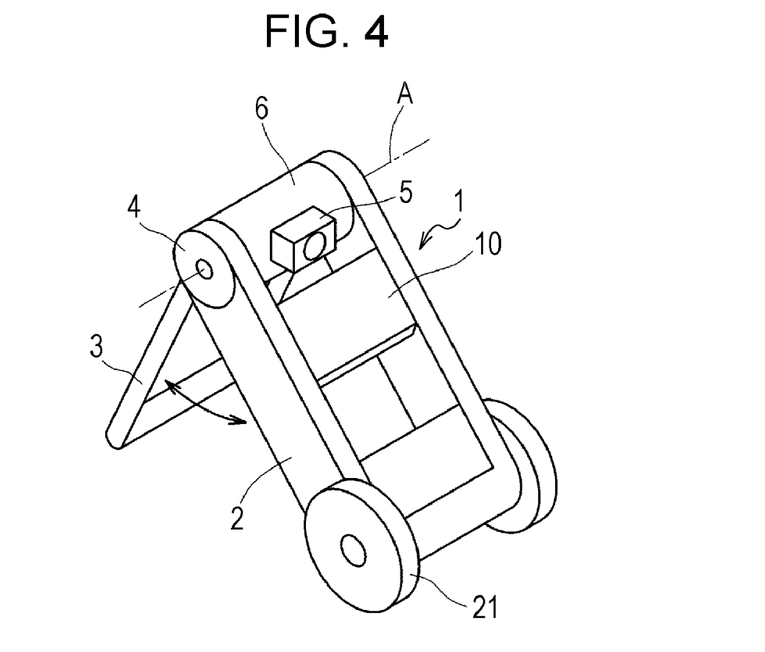
FIG. 4 is a perspective view of the X-ray imaging apparatus according to the second embodiment.

FIGS. 3 and 4 are a side view and a perspective view, respectively, of an X-ray imaging apparatus according to a second embodiment. The same components as those adopted in the first embodiment are denoted by the same reference numerals. While the X-ray generation unit 10 is provided apart from the holding unit 1 with the cable 7 disposed therebetween in the first embodiment, an X-ray generation control unit 10 in the second embodiment is provided between supports of a support leg 2. Further, a pair of moving wheels 21 are provided at a lower end of at least the support leg 2. These moving wheels 21 improve portability.

By virtue of the above-described structure, the X-ray imaging apparatus can be easily moved together with the X-ray generation control unit 10 while the support legs 2 and 3 are closed and the weight is received by the moving wheels 21. Thus, portability is improved.

Third Embodiment

Figure 5:
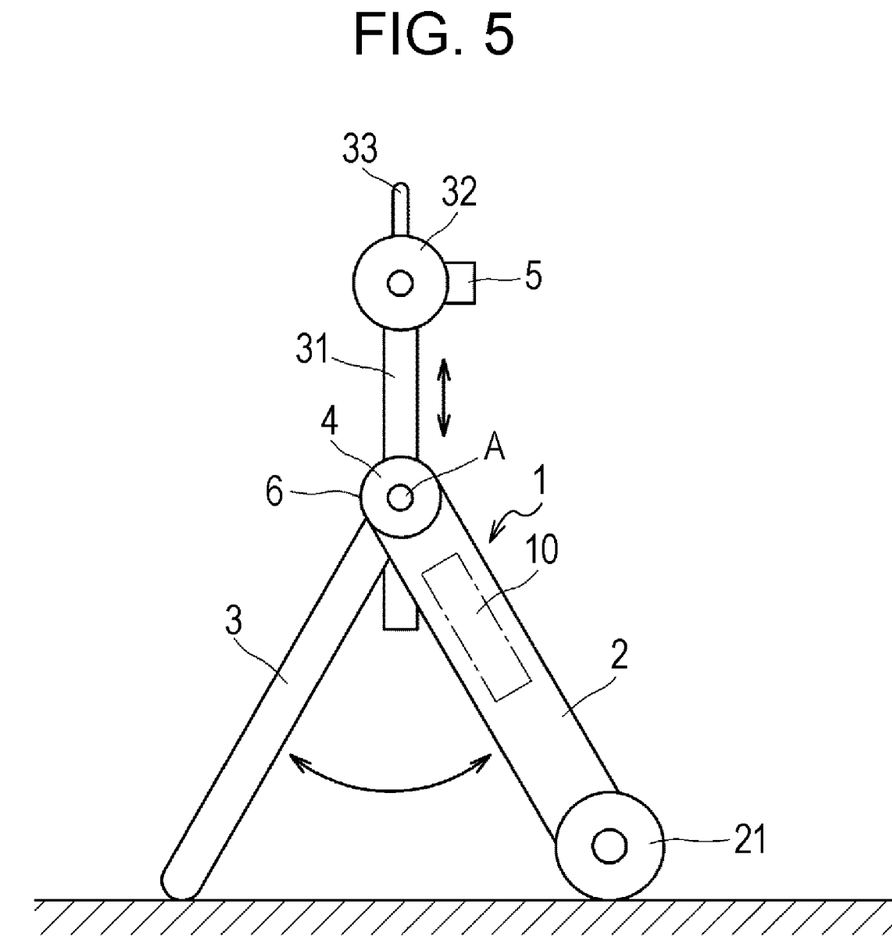
FIG. 5 is a side view of an X-ray imaging apparatus according to a third embodiment.
Figure 6:
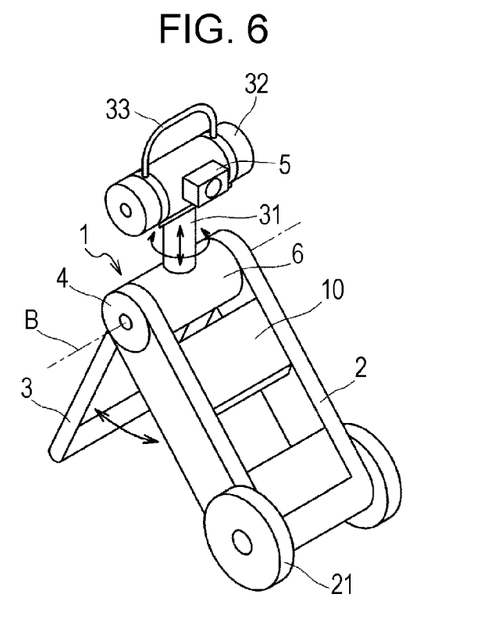
FIG. 6 is a perspective view of the X-ray imaging apparatus according to the third embodiment.

FIGS. 5 and 6 are a side view and a perspective view, respectively, of an X-ray imaging apparatus according to a third embodiment. In the third embodiment, the X-ray imaging apparatus includes a position changing member that moves an X-ray tube 5 of a holding member 6 up and down.

A height adjusting shaft 31 serves as the position changing member, and vertically extends through the holding member 6. At an upper end of the height adjusting shaft 31, a second holding member 32 is provided to hold the X-ray tube 5. The height adjusting shaft 31 can change the height of the X-ray tube 5 relative to the holding member 6 by the frictional force, and can rotate about its axis. Further, the second holding member 32 is provided with a grip portion 33 used for carriage.

Thus, the height of the X-ray tube 5 can be finely adjusted by the height adjusting shaft 31 after being roughly adjusted by the spread angle between the support legs 2 and 3. Moreover, the user can move the X-ray imaging apparatus while holding the grip portion 33.

Fourth Embodiment

Figure 7A:
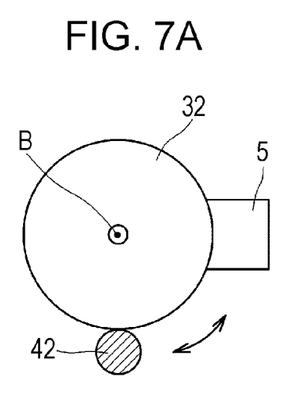
FIGS. 7A and 7B are explanatory views showing the degree of freedom of an X-ray tube according to a fourth embodiment.
Figure 7B:
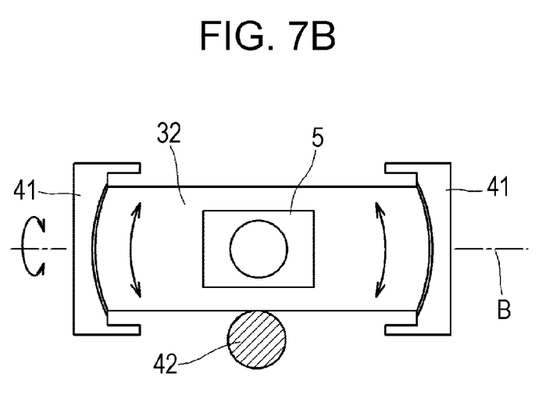

FIGS. 7A and 7B are explanatory views illustrating a fourth embodiment including a unit for changing the radiation direction of an X-ray tube 5 to an arbitrary direction. FIG. 7A is a side view of a movable second holding member 32, as viewed from the side face shown in FIG. 5, and the second holding member 32 can turn on an axis B. FIG. 7B is a front view, as viewed from a direction orthogonal to the axis B shown in FIG. 7A. The second holding member 32 is sandwiched between third holding members 41 at both sides with spherical surfaces disposed therebetween, and can turn on the radiation direction in the directions of the arrows. This allows the X-ray tube 5 to turn through three degrees of freedom, that is, turn on the radiation direction, on the axis B, and on an axis of the height adjusting shaft 31.

Further, the second holding member 32 is provided with at least one weight 42. For example, the gravity of the weight 42 allows the radiation direction of the X-ray tube 5 to easily coincide with the horizontal direction.

Figure 8A:
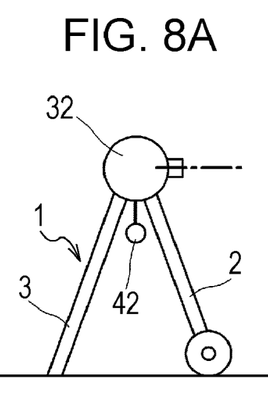
FIGS. 8A and 8B are schematic explanatory views of an X-ray imaging apparatus according to the fourth embodiment.
Figure 8B:
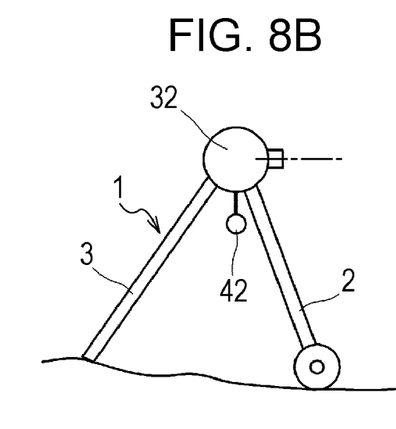

FIGS. 8A and 8B are schematic explanatory views of the X-ray imaging apparatus installed, respectively, on an even ground and an irregular ground. Even on the irregular ground, the X-ray tube 5 can easily point the radiation direction in the horizontal direction because of the weight 42, regardless of the condition of the ground where the apparatus is installed. By placing the weight 42 at an arbitrary position, the radiation direction of the X-ray tube 5 can be changed at an arbitrary angle. When the X-ray imaging apparatus is carried, the weight 42 is locked. When the X-ray imaging apparatus is installed, the weight 42 is unlocked, is adjusted in position in accordance with the radiation direction, and is locked again during image taking.

Figure 9:
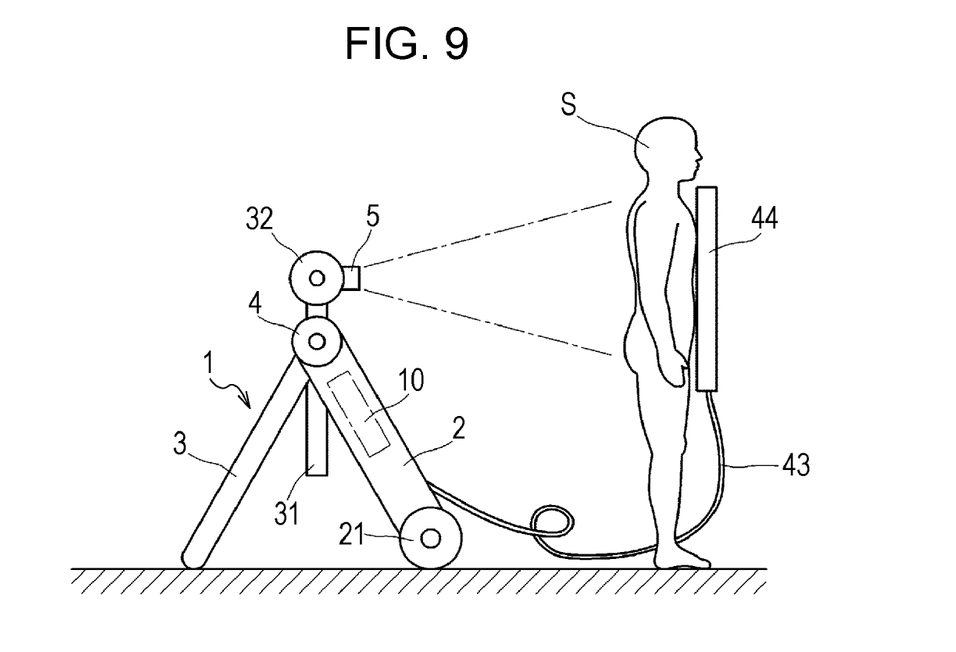
FIG. 9 is an explanatory view showing a state in which an image of a subject in a standing position is taken in the fourth embodiment.

To take an image of a subject S in a standing position, as shown in FIG. 9, with the above-described structure, the X-ray tube 5 is set by the weight 42 to point in the horizontal direction, and the spread angle between the support legs 2 and 3 is adjusted, whereby the height to an image receiving portion 44 connected via a cable 43 to receive X-rays passing through the subject S can be adjusted and an X-ray radiation range can be determined. After that, X-ray image taking is performed.

The image receiving portion 44 receives an X-ray distribution passing through the subject S with detectors arranged in a two-dimensional manner. The image receiving portion 44 is connected to the X-ray generation control unit 10 via the cable 43 or by wireless communication, so that it can be installed at an arbitrary position and can be carried with a range where the connection is possible.

Figure 10:
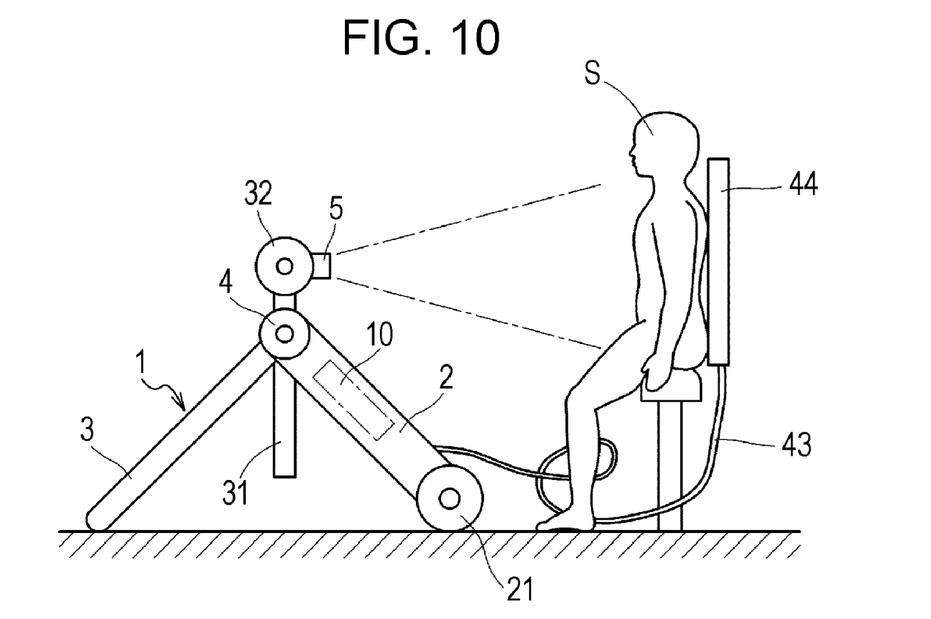
FIG. 10 is an explanatory view showing a state in which an image of a subject in a sitting position is taken in the fourth embodiment.

To take an image of a subject S in a sitting position, as shown in FIG. 10, the X-ray tube 5 is set to point in the horizontal direction and the spread angle between the support legs 2 and 3 is adjusted to adjust the height to the image receiving portion 44 and to determine an irradiation range. After that, image taking is performed.

Figure 11:
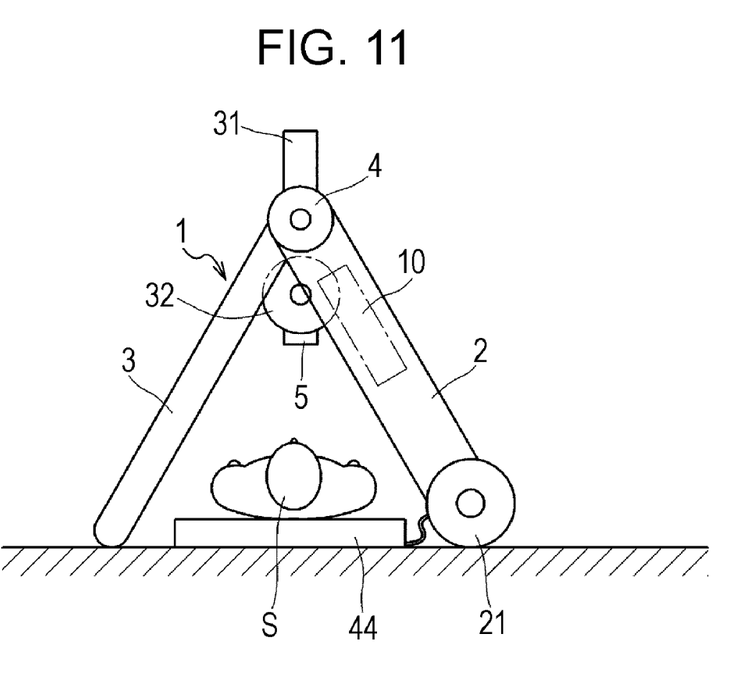
FIG. 11 is an explanatory view showing a state in which an image of a subject lying abed is taken in the fourth embodiment.

To take an image of a subject S lying abed, as shown in FIG. 11, the radiation direction of the X-ray tube 5 is precisely set to point downward, the spread angle between the support angles 2 and 3 and the irradiation range are adjusted in consideration of the body type of the subject S and the position of the image receiving portion 44. After that, image taking is performed. The X-ray imaging apparatus is also applicable to other various body positions, and is aligned easily. This improves operability.

Fifth Embodiment

Figure 12:
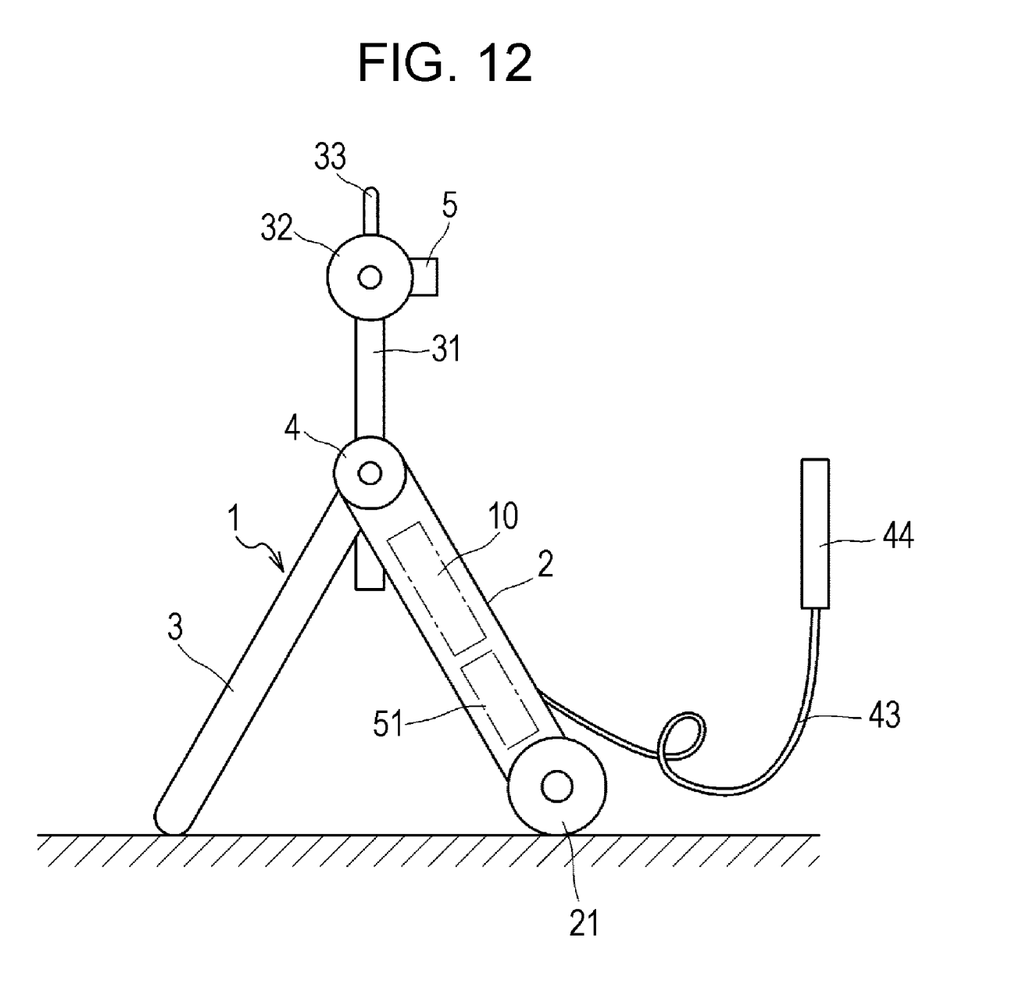
FIG. 12 is a side view of an X-ray imaging apparatus according to a fifth embodiment.
Figure 13:
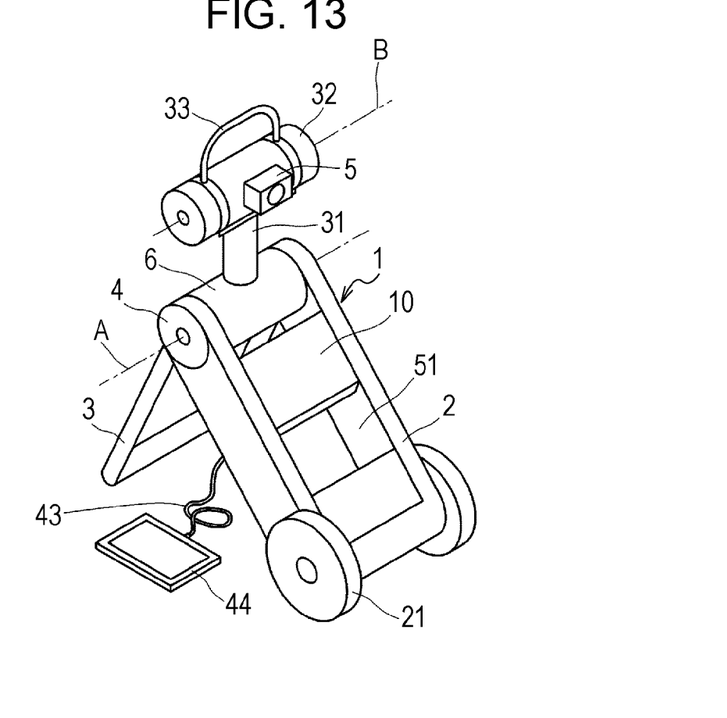
FIG. 13 is a perspective view of the X-ray imaging apparatus according to the fifth embodiment.

FIGS. 12 and 13 are a side view and a perspective view, respectively, of an X-ray imaging apparatus according to a fifth embodiment. In the fifth embodiment, portability is improved by adopting a structure in which an image receiving portion 44 can be stored in an image-receiving-portion storage portion 51 during no use.

This structure allows the image receiving portion 44 to be easily moved together with the X-ray imaging apparatus while being stored in the image-receiving-portion storage portion 51.

Sixth Embodiment

Figure 14:
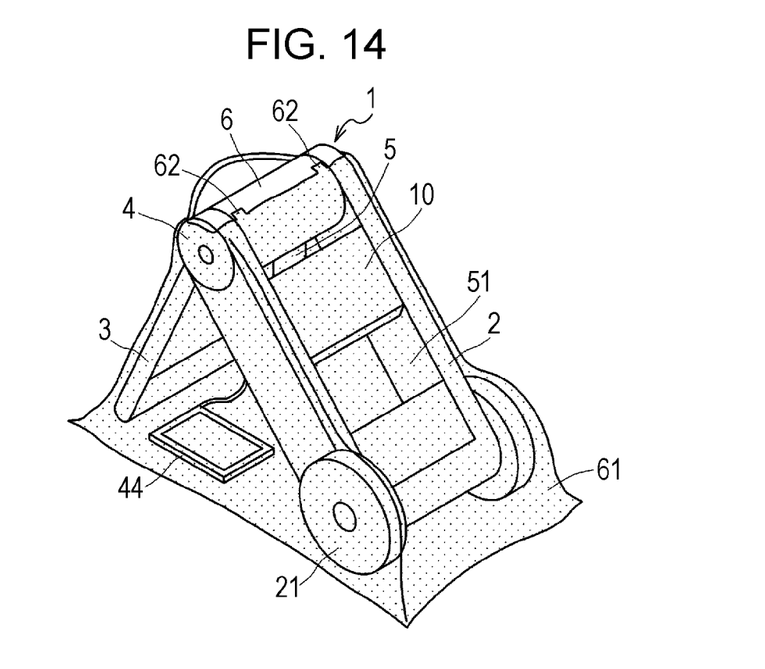
FIG. 14 is a perspective view of an X-ray imaging apparatus according to a sixth embodiment.

FIG. 14 is a perspective view of an X-ray imaging apparatus according to a sixth embodiment. In the sixth embodiment, an X-ray shielding sheet 61 covers support legs 2 and 3 to reduce the risk of exposure.

The X-ray shielding sheet 61 is formed by a flexible sheet containing an X-ray shielding material, such as lead, which has high ability to shield X-rays. The X-ray shielding sheet 61 also has a size such as to substantially entirely cover the apparatus body. Attachment portions 62 of the X-ray shielding sheet 61 are provided in a part of an exterior of an X-ray tube 5 in the X-ray imaging apparatus so that the X-ray shielding sheet 61 hangs to the bottom of the X-ray imaging apparatus to substantially entirely cover the apparatus. Various connecting methods using hooks, snaps, hook-and-loop fasteners, or screws, can be applied to the attachment portions 62.

Since the X-ray shielding sheet 61 is flexible, it can be folded or rolled. The X-ray shielding sheet 61 can therefore be easily stored when not used for image taking, for example, during the standby time or when carried. When the X-ray shielding sheet 61 is made compact, for example, it can be stored with the image receiving portion 44 in the image-receiving-portion storage portion 51 of the support leg 2.

Figure 15A:
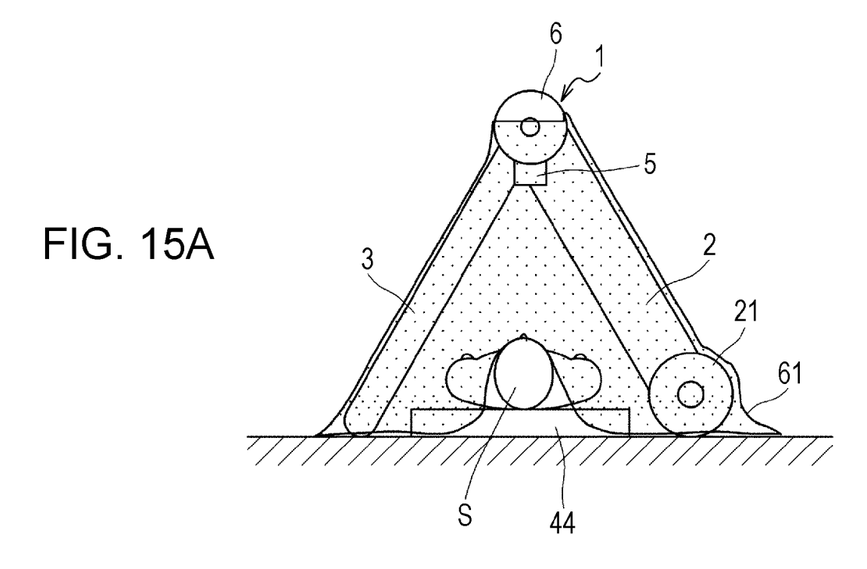
FIGS. 15A and 15B are explanatory views showing a state in which an image of a subject lying abed is taken in the sixth embodiment.
Figure 15B:
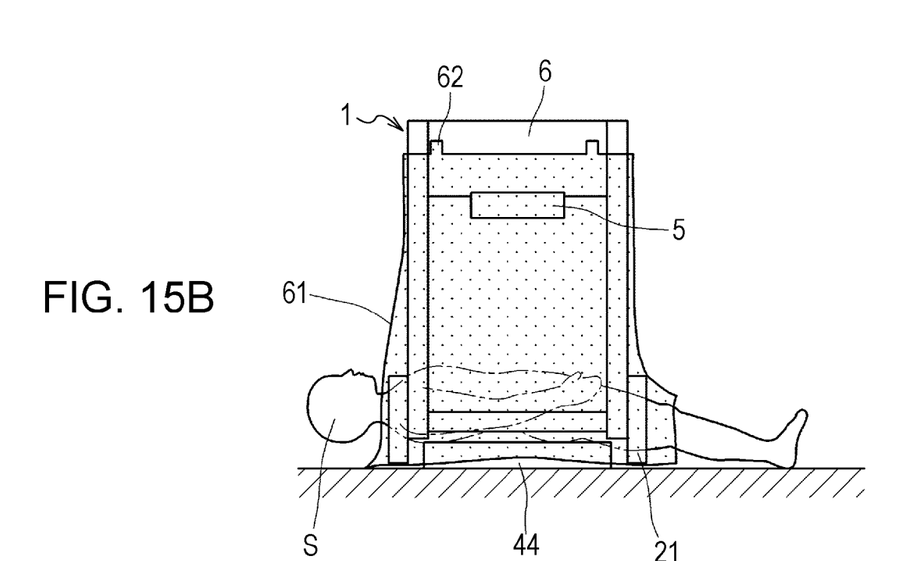

FIGS. 15A and 15B are explanatory views showing a state in which an image of a subject S is taken with the X-ray shielding sheet 61. FIG. 15A is a view of the subject S, as viewed from the head, and FIG. 15B shows a side face of the body of the subject S. An image is taken while the X-ray tube 5 is precisely set to point downward, the image receiving portion 44 is placed between the support legs 2 and 3, and the subject S is lying on an upper surface of the image receiving portion 44.

The X-ray shielding sheet 61 covers the chest of the subject S to be an exposure target and the X-ray imaging apparatus, and prevents applied X-rays from leaking into an external space that is not relevant to image taking. Further, since parts of the subject S other than the exposure target, that is, the head and legs in this case, are placed outside the space covered with the X-ray shielding sheet 61, exposure of these parts is minimized.

Consequently, the X-ray imaging apparatus reduces the risk of exposure of the parts of the subject S other than the exposure target, the X-ray photographer, and other persons.

Seventh Embodiment

Figure 16A:
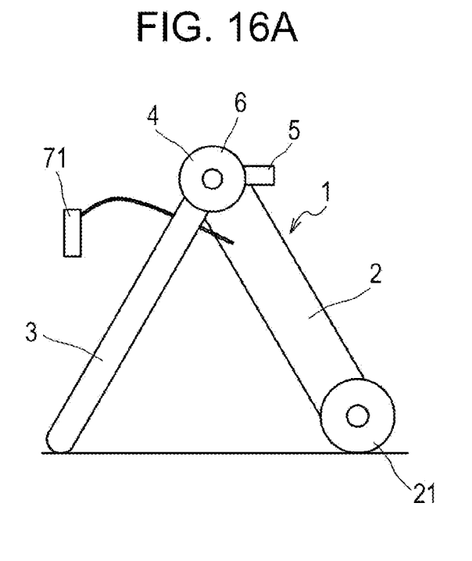
FIGS. 16A and 16B are structural views of an X-ray imaging apparatus according to a seventh embodiment.
Figure 16B:
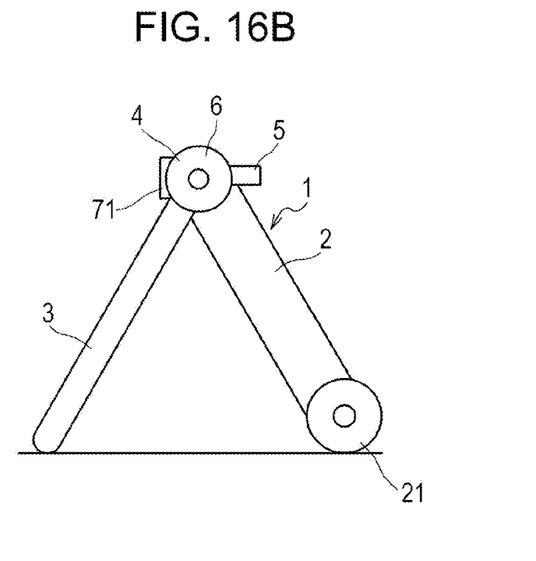
Figure 17:
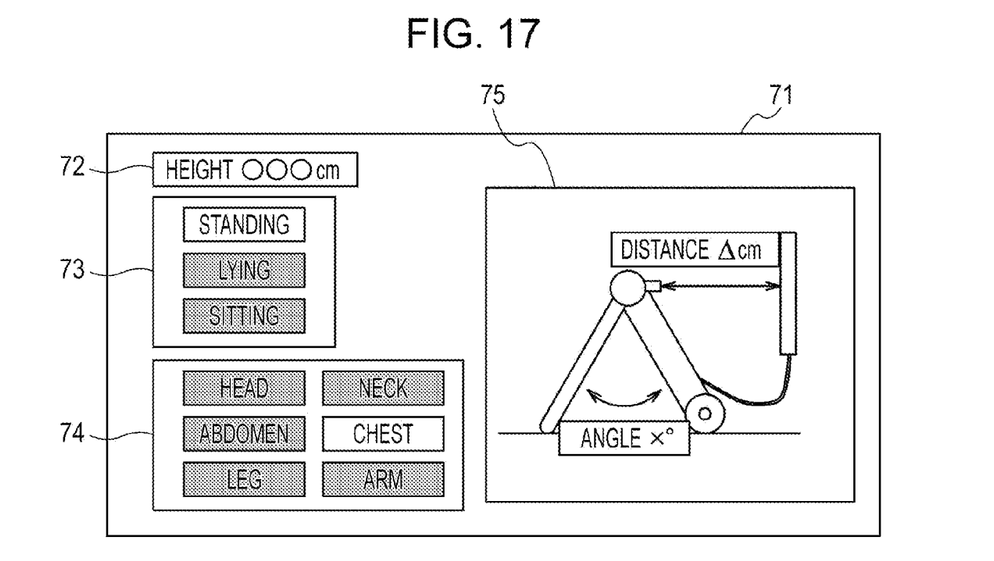
FIG. 17 is a front view of a settings display panel in the seventh embodiment.

FIGS. 16A and 16B are explanatory views illustrating an attachment state of a settings display panel serving as a setting assist unit according to a seventh embodiment, and FIG. 17 is a structural view of the settings display panel. In the seventh embodiment, information about an image taking method and the body type of a subject is entered, and a setting combination of the spread angle between support legs 2 and 3, and the radiation angle and distance of an X-ray tube 5 is displayed on a settings display panel 71 according to the information. This improves operability.

The settings display panel 71 includes a setting information entry unit used to enter information about the image taking method and the body type of the subject S, and a display unit for calculating and displaying a setting combination of the spread angle between the support legs 2 and 3, the X-ray radiation angle, and the distance. The settings display panel 71 is provided near the support legs 2 and 3.

FIG. 16A shows a state in which the settings display panel 71 is placed outside the X-ray imaging apparatus, and FIG. 16B shows a state in which the settings display panel 71 is attached to a holding unit 1.

As shown in FIG. 17, the settings display panel 71 includes a body-type setting portion 72 into which the height of the subject S is entered, an image-taking-position setting portion 73 into which the position of the subject S during image taking is entered, that is, a standing position, a lying position, or a sitting position, and an exposure-target setting portion 74 into which a portion of the body to be exposed is entered.

When the X-ray imaging apparatus is installed, the height of the X-ray tube 5 is obtained as information necessary for installation by data entry into the body-type setting portion 72, the image-taking-position setting portion 73, and the exposure-target setting portion 74. Further, the spread angle between the support legs 2 and 3, the radiation angle of the X-ray tube 5, and the distance between the image receiving portion 44 and the X-ray tube 5 are calculated by the settings display panel 71 in accordance with the height of the X-ray tube 5, and are displayed on a setting-information display portion 75.

The weight and the degree of fatness are also entered into the body-type setting portion 72 as required. This achieves high-precision calculation. By setting up the X-ray imaging apparatus in accordance with this information, it is possible to smoothly initialize or change the image taking conditions.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims priority from Japanese Patent Application No. 2008-223495 (2009/09/01) filed on Sep. 1, 2009, the entire contents of which are hereby incorporated by reference herein.

What is claimed is:

1. An X-ray imaging apparatus comprising:
   an X-ray tube;
   an X-ray generation control unit configured to control the X-ray tube with a controller and a power supply;
   a holding unit configured to hold the X-ray tube,
   wherein the holding unit includes at least two support legs to be spread at an arbitrary angle and a connecting portion configured to turnably connect upper ends of the support legs, and holds the X-ray tube near the connecting portion;
   an entry unit configured to enter information about an image taking method and a body type of a subject; and
   a setting assist unit configured to calculate and display a setting combination of a spread angle between the support legs, an X-ray radiation angle, and a distance on the basis of the information about the image taking method and the body type of the subject.

2. The X-ray imaging apparatus according to claim 1, wherein the holding unit changes a vertical position of the X-ray tube.

3. The X-ray imaging apparatus according to claim 1, wherein the holding unit changes a radiation direction of the X-ray tube.

4. The X-ray imaging apparatus according to claim 1, wherein the support legs hold or accommodate the X-ray generation control unit.

5. The X-ray imaging apparatus according to claim 1, further comprising:
   an image receiving unit configured to detect a distribution of X-rays passing through a subject with detectors arranged in a two-dimensional manner.

6. The X-ray imaging apparatus according to claim 1, wherein a pair of moving wheels are provided at a lower end of at least one of the support legs.

7. The X-ray imaging apparatus according to claim 1, further comprising:
   an X-ray shielding sheet containing an X-ray shielding material, the X-ray shielding sheet being attached to cover the support legs in a state in which the support legs are spread.

* * * * *